United States Patent [19]

de Salis et al.

[11] Patent Number: 5,071,430

[45] Date of Patent: Dec. 10, 1991

[54] SURGICAL INSTRUMENT

[75] Inventors: Sker J. de Salis, Neuchatel; Christian Klaiber, Aarberg, both of Switzerland

[73] Assignee: United States Surgical Corporation, Norwalk, Conn.

[21] Appl. No.: 435,027

[22] Filed: Nov. 13, 1989

[30] Foreign Application Priority Data

Nov. 11, 1988 [CH] Switzerland ..................... 4176/88

[51] Int. Cl.$^5$ ............................................. A61B 17/04
[52] U.S. Cl. .................................... 606/219; 227/155; 227/179; 227/901
[58] Field of Search ................. 606/170, 219; 227/19, 227/155, 156, 179, 180, 901, 902

[56] References Cited

U.S. PATENT DOCUMENTS

| | | |
|---|---|---|
| 3,079,606 | 3/1963 | Bobrov et al. |
| 3,490,675 | 1/1970 | Green et al. |
| 3,499,591 | 3/1970 | Green. |
| 3,675,688 | 7/1972 | Bryan et al. |
| 3,735,762 | 5/1973 | Bryan et al. |
| 4,064,881 | 12/1977 | Meredith. |
| 4,086,926 | 5/1978 | Green et al. |
| 4,111,206 | 9/1978 | Vishnevsky et al. |
| 4,325,377 | 4/1982 | Boebel. |
| 4,429,695 | 2/1984 | Green. |
| 4,606,343 | 8/1986 | Conta et al. |
| 4,610,383 | 9/1986 | Rothfuss et al. |
| 4,784,137 | 11/1988 | Kulik et al. |
| 4,821,942 | 4/1989 | Richards et al. |
| 4,841,888 | 6/1989 | Mills et al. |
| 4,858,608 | 8/1989 | McQuilkin. |
| 4,944,443 | 7/1990 | Oddsen et al. ............ 606/219 X |

FOREIGN PATENT DOCUMENTS

| | | |
|---|---|---|
| 1352554 | 5/1974 | United Kingdom. |
| 1452185 | 10/1976 | United Kingdom. |
| 2048685 | 12/1980 | United Kingdom. |
| 2165559A | 4/1986 | United Kingdom. |

OTHER PUBLICATIONS

Article, Swain, C. P. and Mills, T. N. "An Endoscopic Sewing Machine," *Gastro-Intestinal Endoscope*, 1986, vol. 32, No. 1, pp. 36-38.

Article, Swain, C. P., Brown, G. J. and Mills, T. N. "An Endoscopic Stapling Device: The Development of a New Flexible Endoscopically Controlled Device for Placing Multiple Transmural Staples in Gastrointestinal Tissue", *Gastrointestinal Endoscopy*, 1989, vol. 35, No. 4, pp. 338-339.

Primary Examiner—V. Millin
Assistant Examiner—J. Doyle
Attorney, Agent, or Firm—Thomas R. Bremer; Peter G. Dilworth; Rocco S. Barrese

[57] ABSTRACT

A surgical instrument is disclosed for ablation of organs or parts of organs or for generally cutting and applying surgical clips to the organ or body tissue. The instrument includes an elongated body having a pair of pincer jaws connected to the distal end, one jaw being fixed, and the other jaw being pivotally mounted at its proximal end for movement toward and away from the fixed jaw for gripping body tissue therebetween. A camming tube is provided for retaining the jaws in the closed position to firmly grip tissue. The instrument includes a knife for cutting the organ, and a tool which carries a cam for propelling suture clips into the tissue. The jaws, the knife and the suture clip application tool are all controllable from the proximal end by the surgeon to facilitate remote control when the instrument is inserted into a trocar or other guide tube.

44 Claims, 3 Drawing Sheets

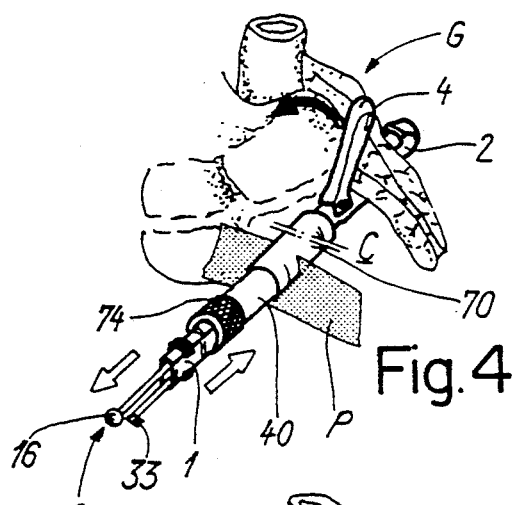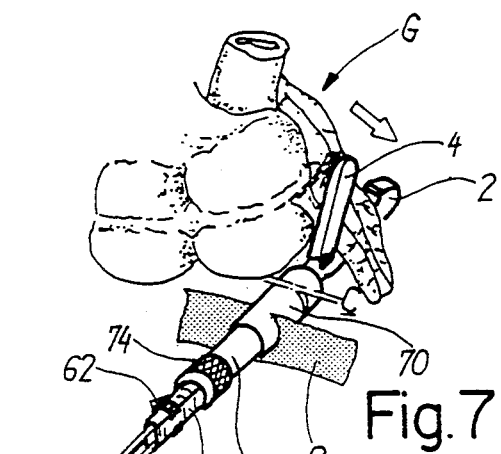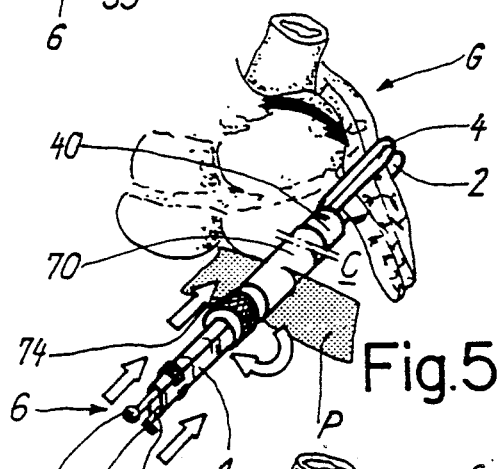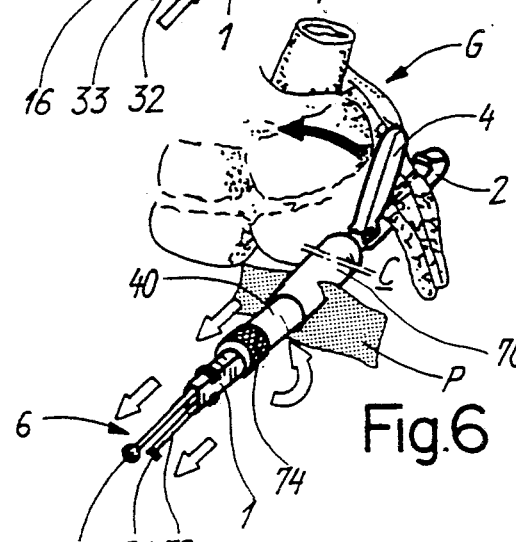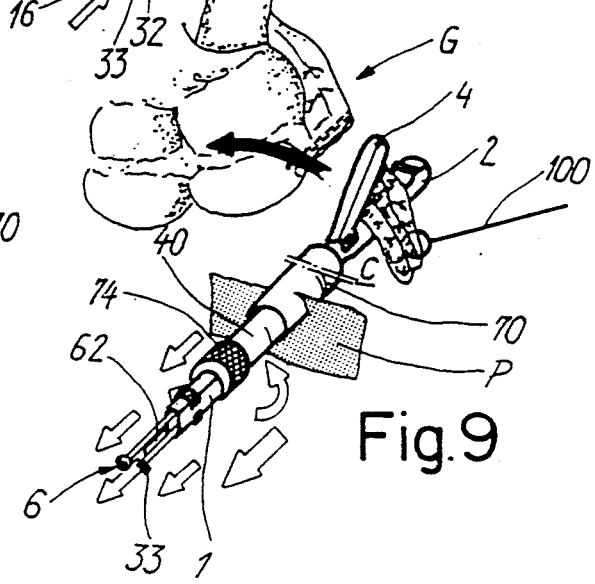

SURGICAL INSTRUMENT

TECHNICAL FIELD

The invention relates to a surgical instrument for the ablation of organs or parts of organs especially involving the pinching, suture clipping and cutting of tissues by endoscopic access.

BACKGROUND OF THE INVENTION

The conventional surgical method used for the ablation of organs consists in making a relatively long cut, operating as needed on the ailing organ, then suturing.

For suturing purposes, ever increasing use is being made of clipping devices instead of hand stitching.

One device for applying suture clips is described in U.S. Pat. No. 4,429,695.

This device comprises a fixed jaw and a mobile jaw, with the mobile jaw being pivotally mounted adjacent its rear end to the corresponding free end of a receiving structure in which the fixed jaw is housed.

These two jaws may be locked relative to one another by means of a handle pivotally mounted to the median part of the mobile jaw and which is able, by means of cam-forming openings to engage on lateral tenons solid with the receiving structure.

However, this known device is not entirely satisfactory because it is so dimensioned as to be usable in a laparotomy (i.e. open procedure) which often necessitates long cuts that may leave extended scars.

For this type of operation, it is now preferred to use the so-called endoscopy technique (laparascopy, thorascopy, etc.).

This operating technique consists in making several orifices that are as small as possible, for example in the abdominal wall, using a trocar, inserting gripping or observation instruments such as an endoscope in some of these orifices, then inserting one or several surgical instruments in the other orifices, all of these instruments being slidably received through tubes passing from the outer wall to the ailing organ.

This technique enables the length of the cut to be considerably reduced. But its application is limited due to the lack of a suitable miniaturized instrument. Also, it requires great dexterity on the part of the surgeon, and rather long operating times.

SUMMARY OF THE INVENTION

An object of the invention is therefore to provide a surgical instrument suitably miniaturized for ablating organs or parts of organs by endoscopy, and yet able to be adequately and precisely manipulated by the surgeon while ensuring an entirely satisfactory gripping force.

The invention therefore relates to a surgical instrument for the ablation of organs or parts of organs by endoscopy involving the pinching, suture clipping and cutting of tissues, said instrument comprising:

a body or receiving structure by which a surgeon can manipulate the instrument, a pair of pincer-forming jaws, one fixed jaw and the other mobile, pivotally mounted relative to one another on said body, pincer control means for controlling the opening and closing of said pincer, means for tightening said pincer such as to enable a part of an organ to be cut to be fixedly held therein, and suture clip applying means and cutting means slidably mounted relative to said body and said jaws respectively to suture and cut said part of the organ, characterized in that the fixed and mobile jaws are pivotally mounted relative to one another at the front end of the instrument body, and said pincer control means is mechanically connected at least to the mobile jaw and extends to the rear end of said instrument body so that said control means are accessible to a surgeon when the instrument is slidably inserted in a trocar tube previously introduced in a patient's body for operation by endoscopy.

According to a particular feature of the invention, the mobile jaw is formed by one arm of an angle lever whose other arm is pivotally mounted preferably at the junction between the fixed jaw and the front end of the instrument body.

According to another feature, the means for controlling the mobile jaw consists of a rigid rod connected to said jaw adjacent the junction between said two arms, this rod being slidably received inside the instrument body.

BRIEF DESCRIPTION OF DRAWINGS

The invention will be better understood from the following description with reference to the accompanying drawings given solely by way of example, and in which:

FIGS. 4 to 9 show different phases of a surgical operation carried out using the instrument of FIGS. 1 to 3.

DETAILED DESCRIPTION

Figure 1:
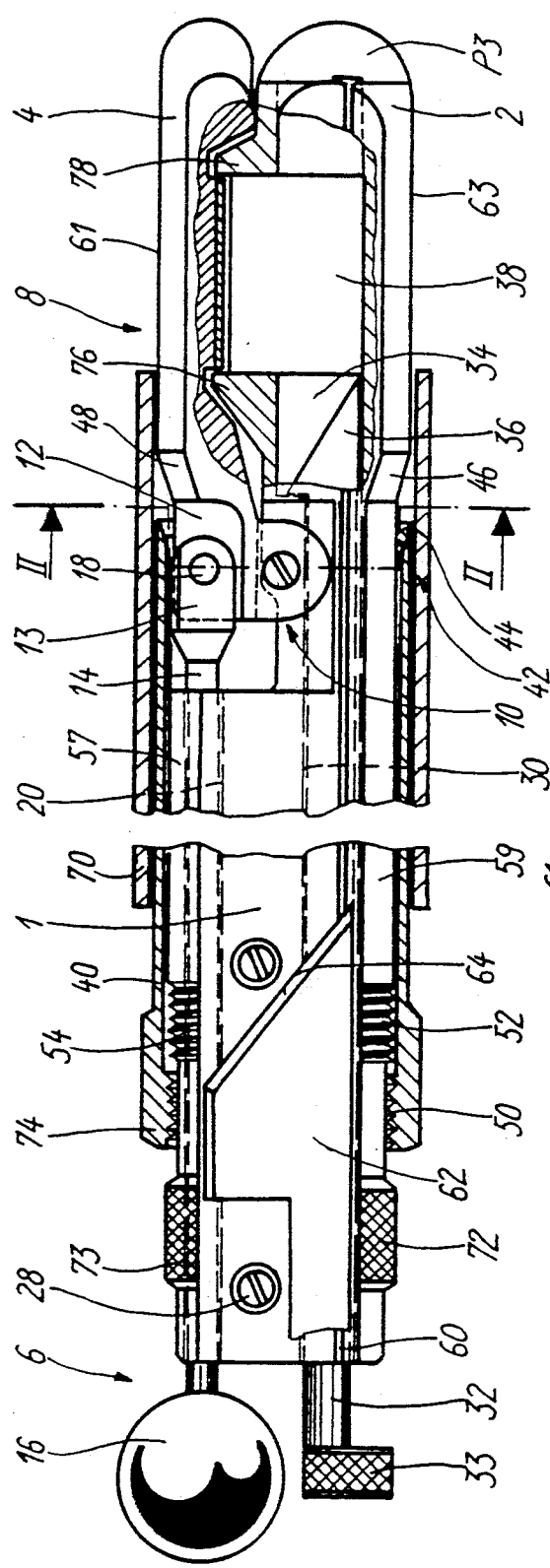
FIG. 1 is a side view partly in cross-section of an instrument according to the invention.
Figure 2:
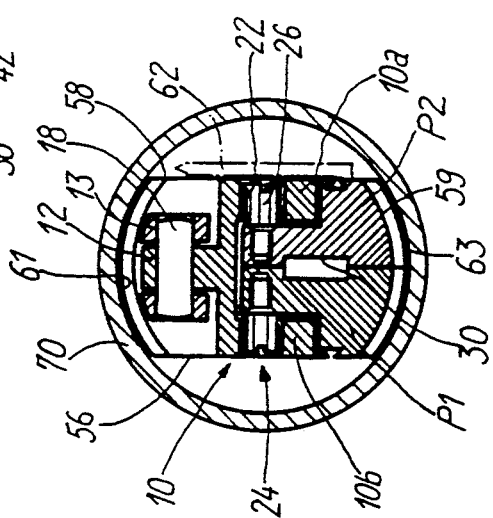
FIG. 2 is a cross-sectional view along line II—II of FIG. 1 showing also in broken lines a knife able to slide along the instrument body.
Figure 3:
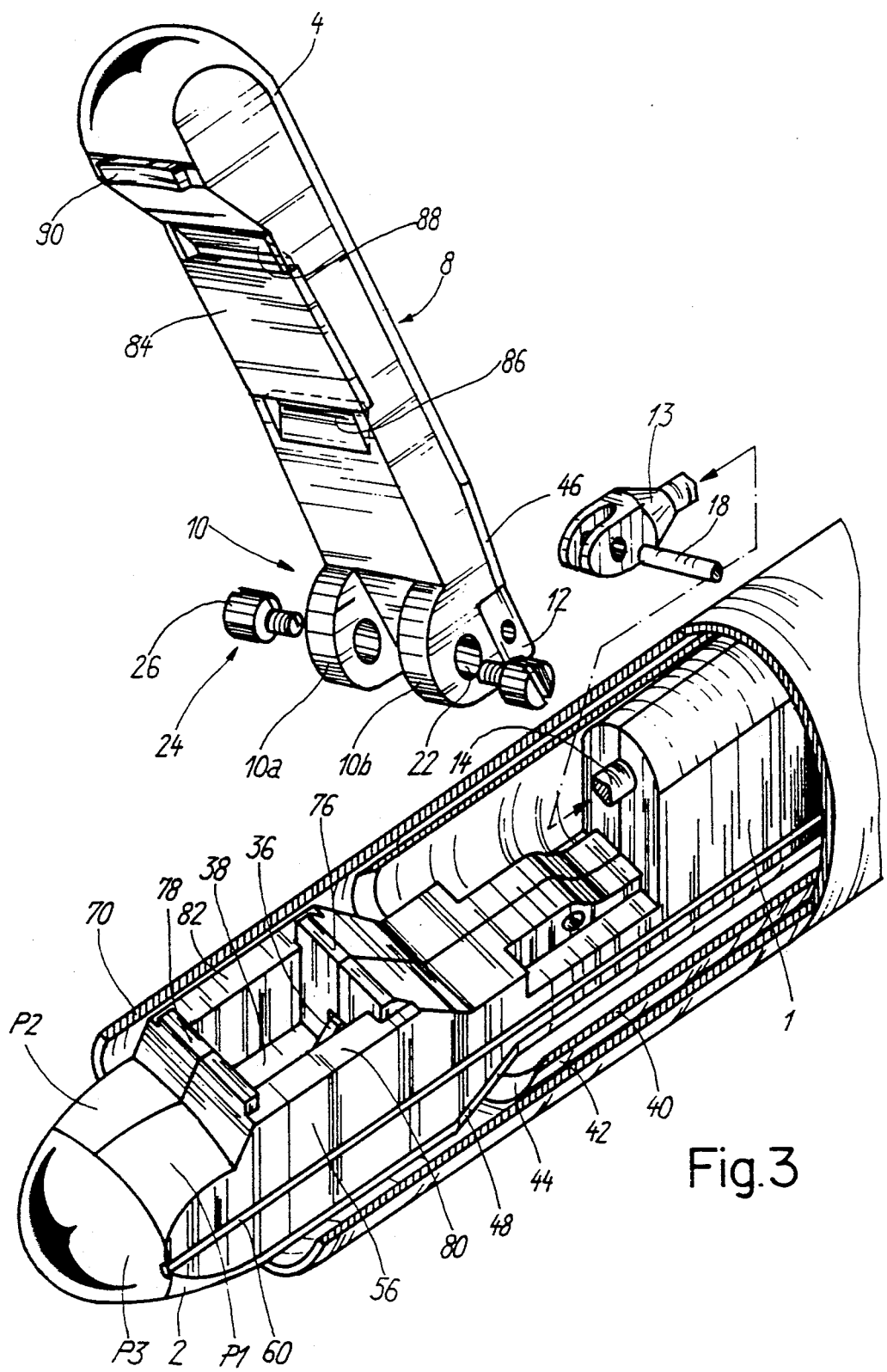
FIG. 3 is an exploded perspective view of the instrument shown in FIGS. 1 and 2 but in which the relative dimensions of the different parts are not exactly to scale.

The surgical instrument shown in FIGS. 1 to 3 comprises a body or receiving part 1 provided at its front end with a fixed jaw 2 and a mobile jaw 4, pivotally mounted relative to one another.

The mobile jaw 4, actuable by control means 6 issuing out of the rear end of the body 1, is in the form of an angle lever. One arm, 8, of this lever includes parts adapted to pinch tissues and forms the mobile jaw 4.

The other arm, 10, of this angle lever is pivotally mounted, at the junction of the fixed jaw 2 and the front end of body 1, on the rear part of the fixed jaw 2.

As shown in FIG. 2, the pivotal arm 10 forming the rear part of mobile jaw 4 has in cross-section approximately the shape of an inverted "U" from the bridging part of which extends a rib 12.

This rib 12 receives, by a clevis connection, a yoke 13 extending from a rigid rod 14 (see FIG. 3). With a spherical knob 16 screwed on its end, this rod 14 constitutes the control means 6 of mobile jaw 4.

In this way, the rod 14 is operatively connected to the mobile jaw 4 adjacent the junction between the two arms 8 and 10, by means of a pin 18 pivotally connecting the yoke 13 to rib 12.

The rod 14 is freely slidably received inside the body 1 in a through opening 20.

The lever arm 10 has two cheeks 10a and 10b in U-configuration having transverse bores 22 each receiving a pivot pin 24 solid with the fixed jaw 2. Each pin 24 is for example formed by a screw threadably engaged in a screw thread in the fixed jaw 2, this screw having a head 26, preferably ground true, that engages preferably with a sliding fit in one of the bores 22.

The "U" at the rear part of the mobile jaw 4 advantageously fits over a corresponding rear part of the fixed jaw 2.

The instrument body, as well as the fixed jaw 2, which is of the same material therefrom, are made of two pieces P1 and P2 that can be assembled in side-by-side relation along their length.

The described U-assembly on the rear part of the fixed jaw 2 therefore contributes to holding the pieces P1 and P2 in fixed side-by-side relationship.

Of course, these parts P1 and P2 may have in their facing sides complementary pins and recesses that cooperate to center the parts.

If the instrument according to the invention is not intended to be re-used, but must be thrown away after having been used in a surgical operation, the facing sides of the parts P1 and P2 can be stuck together using a suitable glue.

But if the instrument must be dismantled after use to be cleaned and sterilized, countersunk screws 28 may be threadably engaged in corresponding screw threads at suitable locations on the instrument body 1 and the fixed jaw 2.

The two screws 24 forming pivot pins for the mobile jaw 4 may be replaced by a bolt passing through a bore in the rear part of the fixed jaw 2, this bolt and its nut being suitably ground true. As the manner of fitting these constructional parts is well known to persons skilled in the art, such parts have not been shown in detail.

Inside the instrument body 1 and the fixed jaw 2 is a first longitudinal guide cavity 30 that receives and guides a tool 32 for applying suture clips. This cavity 30 extends from end to end of the body 1, and also all the way along the fixed jaw 2, and preferably has a rectangular cross-section.

The cavity 30 therefore communicates at one end with the outside at the rear end of the instrument body 1 and at its other end with a recess 34 in the fixed jaw 2, this recess extending to the front end of the fixed jaw and preferably being higher than the cavity 30.

The rear end 33 of tool 32 can thus project out of the rear end of body 1, whereas the front end of tool 32 carries a cam 36 for propelling suture clips, lodged in the recess 34.

This recess 34 communicates with a chamber 38 provided in the fixed jaw 2.

The chamber 38 is configured to receive a rechargeable supply of suture clips.

This supply of suture clips can be in a magazine, not shown. The orientation of the suture clips in the chamber 38 in relation to a section of an organ G to be cut is schematically represented in FIGS. 6 to 9. These suture clips are generally arranged in two longitudinally-offset parallel rows disposed parallel to the instrument.

The cavity 30, recess 34 and chamber 38 form together an orifice of variable cross-section able to receive the suture clip applying means.

The illustrated surgical instrument further comprises means for holding together the two pincer-forming jaws 2 and 4 in a position in which they grip the tissues of an organ.

These clamping means are formed by a tube 40 coaxial with and slidably engaged around the body 1. A front or bearing end 42 of this tube 40 is able to engage with the rear part of the fixed and mobile jaws 2, 4 when these jaws are closed, as shown in FIG. 1.

The inside of the front end 42 of tube 40 has an at least partly frusto-conical part 44 configured to fit against corresponding partly frusto-conical regions 46 and 48 provided respectively on the rear parts of the fixed and mobile jaws 2, 4.

This clamping tube 40 further comprises an internal threading 50 threadably engageable on externally threaded sectors 52 and 54 arranged at least partly around the outer periphery of body 1.

The length of the clamping tube 40 is selected so that the rear end of this tube 40, which has an integral enlargement 74 of the same material therefrom and forming a control ring, is accessible to a surgeon when the instrument is inserted in a trocar tube 70, the instrument being adapted to be slidably received in this tube 70.

The body 1 and the pincer 2,4 when closed have in transverse cross-section a partly circular external periphery having lateral flats 56, 58 along the entire length of the instrument.

These flats 56, 58 each form a lateral face in which a longitudinal groove 60, for example a dove-tail groove, can be provided.

FIG. 2 shows only two grooves 60, but several grooves could be provided on one or both of the flats 56 and 58.

This longitudinal groove 60 is adapted to receive a knife 62 that can be inserted from the rear end of body 1. The knife 62 is long enough for its blade 64 to reach a region where tissues are gripped between the two jaws 2 and 4 while being controlled from the rear end of the instrument body 1.

The diametral dimensions of the instrument body 1 at the location of its circular parts 57 and 59 are smaller than the corresponding diametral dimensions of the circular parts 61 and 63 of the pincer formed by the jaws 2 and 4 when these are brought together.

Because of this, when the instrument is inserted in a guide tube 70 passing through the patient's tissues and which is left in place during the operation in the region of the abdominal wall, the clamping tube 40 can freely slide through the space between the body 1 and the tube 70 coaxial therewith.

Moreover, to facilitate manipulation of the illustrated instrument body 1 by a surgeon, this body 1 has two removable, knurled sectors 72 and 73.

When these sectors 72 and 73 are removed, the clamping tube 40 can be slid rearwardly to enable complete dismantlement of the instrument.

The fixed jaw 2 and mobile jaw 4 are arranged to have two projecting lugs 76 and 78 between which tissues to be sutured can be engaged.

These lugs 76 and 78 project upwards from the fixed jaw 2 towards the mobile jaw 4 to define a suture-clip-applying region. The lugs 76 and 78 extend transversally across the fixed jaw 2 part of the way across its width.

Thus, between and on either side of the lugs 76, 78 extend two tissue-receiving planes 80, 82.

The mobile jaw 4 has two recesses 86 and 88 arranged to receive the lugs 76 and 78, respectively.

Between the recesses 86, 88 is a plate 84 against which, during the suture clip application step, the clips contained in the chamber 38 are pressed so as to close.

The chamber 38 opens between the lugs 76, 78 opposite the plate 84 of the mobile jaw 4, i.e. in the region for suturing tissue with clips.

To define the distance between the fixed and mobile jaws 2, 4 available for pinching tissues, a fixed or adjustable abutment 90 is provided, preferably on the front end of the mobile jaw facing the corresponding end of the fixed jaw. Furthermore, on the front end of the fixed jaw is secured (by glueing, screwing or the like) a partly-spherical end cap P3 to avoid injuring organs when the instrument is inserted in the abdominal wall through a trocar tube 70.

The cap P3 closes the entrance orifice of the means for applying suture clips, namely the recess 34. It also functions as a protection and abutment element defining an end-of path stop for the pointed front edge of the cam 36, preventing it from leaving the instrument and from causing damage to the tissues.

FIGS. 4 to 9 show the illustrated instrument in its different operating phases.

In all of these operating phases, the externally-knurled rear part 74 of the clamping tube 40, the spherical cap 16 forming control means 6 for the pincer 2, 4, the rear part 33 of tool 32, and the knife 62 are all externally accessible for manipulation by a surgeon from outside the abdominal cavity C shown partly in FIGS. 4 to 9.

Operation of the described instrument is as follows:

Firstly, a trocar tube 70 is inserted in conventional manner into abdominal cavity C through the abdominal wall P, shown partly.

Then, the instrument with its jaws 2, 4 closed is inserted in the tube 70. The entire instrument, namely the jaws 2, 4 then the body surrounded by the clamping tube 40, is slidably passed in the guide tube 70 towards the organ G to be operated on.

After the jaws 2, 4 have passed through the front end of guide tube 70 (FIG. 4), the control means 6 of the mobile jaw 4 is pulled rearward to open the jaws 2, 4 around tissues of the organ G.

As shown in FIG. 5, as soon as the tissues are engaged in the suture clip application region (lugs 76, 78 of jaw 2), the control means is pushed forward to close the mobile jaw 4 on the fixed jaw 2, and the clamping tube 40 is pushed towards the closed jaws until the internal threading 50 (FIG. 1) of the clamping tube 40 comes to the threaded sectors 52, 54 of the instrument body 1.

At this moment, the clamping tube 40 is turned to engage the threads 50, 52 and 54 until the frusto-conical parts 44 of the clamping tube 40 and 46, 48 of the jaws 2, 4 contact one another with a sufficient resisting torque. Because the angle of the frusto-conical parts is arranged so as to provide a self locking effect, the jaws 2, 4 will be held locked against one another, maintaining fixedly compressed therebetween a first section of the organ G to be attached by suture clips.

When the tissues are firmly held in place, the end 33 of tool 32 is pushed forwards to make the cam 36 push up the suture clips contained in the fixed jaw 2.

Then, as shown in FIG. 6, the tool 32 is pulled out, the clamping tube 40 unscrewed and pulled until the jaws 2, 4 are freed. The control means 6 is then pulled out to open the mobile jaw 4.

At this point, the instrument could be withdrawn from the abdominal cavity to be reloaded, or could be replaced by an identical second instrument loaded with suture clips.

When a first row of suture clips has been put in place, the instrument is moved sidewards, usually by inclining it quite substantially, until a new part of the tissues is engaged between the jaws 2 and 4 (FIG. 7).

Once the pincer 2, 4 is adequately positioned with a part of the tissues in the clip-applying region, the jaw is closed by once again forwardly actuating the control means 6 (FIG. 8), then locked by moving forward the clamping tube 40 and screwing it to bring the self-locking frusto-conical parts into cooperation. A new part of the organ G is thus firmly held in place, and the clip-applying means is once again actuated by pushing the tool 32.

When the second row of suture clips has been put in place, the knife 62, which is preferably pre-positioned alongside the body 1 or could be inserted during the operation, is manipulated. A guide part of the knife 62 is engaged in the lateral groove 60 (FIGS. 1 and 3) so that the knife can be slid inside the clamping tube 40, laterally alongside the body 1, to bring its cutting edge 64 between the two previously-applied rows of suture clips.

As shown in FIG. 9, the knife 62 is then withdrawn. The clamping tube 40 is unscrewed by acting on the ring 74 and then pulled out, and the control means 6 of the mobile jaw 4 as well as the tool 32 are pulled out. Ablation having taken place, the cut part of the organ G is picked up by a gripping device 100 introduced through the abdominal wall via another trocar tube. The jaws 2, 4 are then brought together by actuating the control means 6 and the described and illustrated surgical instrument is removed from the abdominal cavity C through the guide tube 70. This guide tube 70 is then removed from the abdominal wall P. In this method, a first row of suture clips was put in place, then the instrument moved to apply a second row of clips beside the first row. This enables the surgeon, at each stage of the operation, to check the quality of the clip attachments. A cut is then made between the two rows of clips to detach the ailing part of the organ G. Any risk of an effusion of blood in the abdominal cavity C is thereby avoided because it is possible to check the quality of the clip attachments.

Furthermore, because of the particularly compact construction of the instrument body 1 and of the jaws 2, 4, the instrument can be precisely manipulated by a surgeon. Moreover, the described clamping means make the jaws clamp well against one another which of course helps to perform the suturing attachments more efficiently.

What is claimed is:

1. A surgical instrument for driving surgical fasteners into body tissue which comprises:
 a) a body having a distal end and a proximal end and defining an endoscopic portion at said distal end;
 b) a pair of jaws positioned at said distal end of said body, a first jaw fixed with respect to said body and a second jaw pivotally mounted at the proximal end thereof for movement between an open position whereby at least the distal end of said second jaw is spaced from said first jaw and a closed position whereby said second jaw is in close cooperative alignment with said first jaw;

c) means for controlling the open and closed positions of said second jaw with respect to said first jaw from the proximal end of said body;

d) means positioned about at least a portion of said body and slidable between a proximal position whereby said second jaw may be pivoted to said open position with respect to said first jaw, and a distal position in close cooperative alignment at least with said second jaw whereby tissue positioned therebetween may be gripped by said jaws; and e) means associated with said body for applying surgical fastener means to body tissue gripped between said jaws.

2. A surgical instrument according to claim 1, wherein said second jaw is formed by a first arm of an angle lever pivotally mounted by a second arm at the junction between said fixed jaw and the distal end of said body.

3. A surgical instrument according to claim 2, wherein said means for controlling said second jaw comprises a rigid rod connected to said second jaw adjacent the junction between said first and second arms, said rod being slidably received within said body.

4. A surgical instrument according to claim 1, wherein a proximal part of said second jaw is comprised at least in part of a member having an inverted substantially "U" shaped configuration having two arms positioned over a proximal part of said fixed jaw, said arms having respective lateral bores each housing a pivot pin connected to said fixed jaw.

5. A surgical instrument according to claim 4, wherein said two pivot pins comprise screws having heads and being slidably received in the corresponding bores of the arms of said inverted substantially "U" shaped member.

6. A surgical instrument according to claim 4, wherein said elongated body and said fixed jaw are made of two parts assembled in side-by-side relationship.

7. A surgical instrument according to claim 6 wherein said inverted U-shaped member of said second jaw is configured and dimensioned to assist retaining said two parts of said fixed jaw when said second jaw is pivoted to the closed position.

8. The surgical instrument according to claim 7 wherein said means to predetermine the position of said second jaw relative to said first jaw comprises abutment means attached to said second jaw and adapted to engage said first jaw when said second jaw is closed.

9. The surgical instrument according to claim 8 wherein said abutment means is a member attached to the distal end of said second jaw and extending transversely thereof, the thickness of said abutment means determining the space between said first and second jaws when said second jaw is closed.

10. The surgical instrument according to claim 9 wherein said thickness of said abutment member is adjustable to facilitate selective positioning of said second jaw with respect to said first jaw.

11. The surgical instrument according to claim 10 wherein said thickness of said abutment member is fixed to thereby predetermine the position of said second jaw with respect to said first jaw when in the closed position.

12. A surgical instrument according to claim 1, wherein said slidable means comprises a clamping tube slidably mounted about said body, said tube having a distal end having an internal at least partly frusto-conical surface portion adapted to bear against corresponding frusto-conical portions provided at the proximal end of said first jaw and said second jaw respectively.

13. A surgical instrument according to claim 12, wherein said clamping tube includes internal threads adapted to threadably engage with external threaded sectors of said body.

14. A surgical instrument according to claim 12, wherein said instrument body and said first and second jaws have a part-circular periphery and include at least two longitudinal flats.

15. A surgical instrument according to claim 14, wherein said circular regions of said body include external diametral dimensions less than the dimensions of said circular regions of said jaws when said jaws are brought together, to allow said clamping tube to pass between said body and a trocar guide tube.

16. The surgical instrument according to claim 12 wherein said frusto-conical surface portions on said clamping tube and said frusto-conical surface positions on said jaws are configured to cause said jaws to be self-locking when engaged by said clamping tube.

17. The surgical instrument according to claim 16 wherein said clamping tube includes internal threads adapted to be threadably engaged with corresponding mating threads on said body to facilitate advancing said clamping tube distally to cause the position of said second jaw to be self-locked in a closed position with respect to said first jaw.

18. A surgical instrument according to claim 1, wherein said fixed jaw is made of the same material as said body.

19. A surgical instrument according to claim 1, wherein said body and said first jaw are comprised of two parts positioned in side-by-side relationship.

20. A surgical instrument according to claim 1, wherein said two parts forming said body and said fixed jaw are held fixedly attached with said parts engaging in said inverted substantially "U" shaped section of said second jaw.

21. A surgical instrument according to claim 1, wherein said body and said fixed jaw have a first longitudinal orifice of substantially rectangular cross-section, in which a tool is slidably received, said tool having a first end which protrudes from said proximal end of said body and a second end carrying a cam for feeding surgical fastener means.

22. A surgical instrument according to claim 21, wherein said orifice further includes a chamber in said fixed jaw for receiving a rechargeable magazine of surgical fastener means.

23. A surgical instrument according to claim 22, wherein said chamber extends into a surgical fastener application region facing a plate on said second jaw for closing said surgical fastener means.

24. The surgical instrument according to claim 1 wherein said body is elongated.

25. A surgical instrument according to claim 24, wherein said body and said fixed jaw comprise at least one longitudinal guide groove on at least one lateral surface thereof for holding a knife.

26. The surgical instrument according to claim 25 wherein said slidable means is a clamping tube adapted to engage the proximal portion of each said first and second jaws in a manner to retain said jaws in the closed position to facilitate gripping tissue therebetween.

27. The surgical instrument according to claim 26 wherein said clamping tube comprises control means extending to the proximal end of said body to facilitate user access therefor.

28. The surgical instrument according to claim 27 wherein a knife for cutting body tissue is supported by said lateral groove.

29. The surgical instrument according to claim 28 wherein said knife comprises control means extending to the proximal end of said body to facilitate user access therefor.

30. A surgical instrument according to claim 24, wherein one of said jaws, comprises at least two lugs for receiving therebetween tissues of an organ or body tissue (G) to be cut.

31. A surgical instrument according to claim 24, further comprising an abutment on said second jaw defining a gap between said two jaws for pinching body tissue therebetween.

32. A surgical instrument according to claim 1, wherein said proximal end of said elongated body comprises two removable knurled sectors for holding said body said knurled sectors being movable to allow removal of said clamping tube by sliding same along said body.

33. A surgical instrument according to claim 1 wherein said proximal end of each said first and second jaws has a frusto-conical shape and at least a portion of said slidable member has a corresponding frusto-conical shape adapted to engage said proximal frusto-conical shaped portions of said first and second jaws.

34. The surgical instrument according to claim 1 wherein means is provided on said second jaw to predetermine the position of said second jaw with respect to said first jaw when said second jaw is in the closed position.

35. The surgical instrument according to claim 1 wherein said slidable means is a clamping tube adapted to engage said proximal portion of each said first and second jaws in a manner to retain said jaws in the closed position to facilitate gripping tissue therebetween.

36. The surgical instrument according to claim 35 wherein said clamping tube extends to the proximal end of said body to facilitate fixing the position of said first jaw with respect to said second jaw from the proximal end of said body.

37. A surgical instrument for driving surgical fasteners into body tissue which comprises:
 a) a body having a distal end and a proximal end and defining an endoscopic portion at said distal end;
 b) a pair of pincer forming jaws connected to said distal end of said body, a first jaw fixed with respect to said body and a second jaw pivotally mounted at the proximal end of said second jaw for movement between an open position whereby at least the distal end of said second jaw is spaced from said first jaw and a closed position whereby said second jaw is in close cooperative alignment with said first jaw;
 c) means for controlling the open and closed positions of said second jaw with respect to said first jaw from the proximal end of said body;
 d) camming means positioned about at least a portion of said body and having a camming surface at the distal end thereof, said camming means being slidable between a proximal position whereby said second jaw may be pivoted to said open position with respect to said first fixed jaw, and a distal position whereby said camming surface engages the proximal end of at least said second jaw to cause said jaws to be positioned relative to each other whereby tissue positioned therebetween may be firmly gripped by said jaws; and
 e) means associated with said body for applying surgical clip means to body tissue gripped between said jaws.

38. A surgical instrument according to claim 37 wherein said camming surface on said camming means is frusto-conical.

39. The surgical instrument according to claim 38 wherein said first and second jaws define frusto-conical surfaces at their proximal ends to be engaged by said camming surface of said camming means.

40. The surgical instrument according to claim 39 wherein said frusto-conical surfaces are such as to cause said jaws to be self-locking due to the engagement at least with said first jaw by said camming means.

41. The surgical instrument according to claim 40 wherein said clamping tube includes internal threads adapted to be threadably engaged with corresponding mating threads on said body to facilitate advancing said clamping tube distally to cause the position of said first jaw to be self-locked in a closed position with respect to said first jaw.

42. A surgical instrument for driving surgical fasteners into body tissue which comprises:
 a) an elongated body having a distal end and a proximal end and defining an endoscopic portion at said distal end;
 b) a pair of pincer forming jaw connected to said distal end of said endoscopic portion, a first jaw having a frusto-conical surface portion at the proximal end and fixed with respect to said endoscopic portion and a second jaw having a frusto-conical surface portion at the proximal end and being mounted at the proximal end thereof for movement between an open position whereby at least the distal end of said second jaw is spaced from said first jaw and a closed position whereby said second jaw is in close cooperative alignment with said first jaw;
 c) means for controlling the open and closed positions of said second jaw with respect to said first jaw from the proximal end of said body;
 d) camming means positioned about at least a portion of said body and having a camming surface at the distal end thereof, said camming means being slidable between a proximal position whereby said second jaw may be moved to said open position with respect to said first jaw, and a distal position whereby said camming surface engages the proximal ends of said first and second jaws to cause said jaws to firmly pinch body tissue therebetween whereby tissue positioned therebetween may be firmly gripped by said jaws;
 e) a knife movable between proximal and distal positions for cutting body tissue gripped between said jaws, said knife having means to control the position thereof from the proximal end of said elongated body; and
 f) means positioned within said body for applying surgical fastener means to body tissue gripped between said jaws.

43. The surgical instrument according to claim 42 wherein said frusto-conical surfaces are such as to cause said jaws to be self-locking due to the engagement at least with said first jaw by said camming means, said instrument further comprising a trocar guide tube for reception of said endoscopic portion when said trocar guide tube is positioned within a body portion.

44. The surgical instrument according to claim 43 wherein said clamping tube includes internal threads adapted to be threadably engaged with corresponding mating threads on said body to facilitate advancing said clamping tube distally to cause the position of said second jaw to be self-locked in a closed position with respect to said first jaw.

* * * * *